(12) United States Patent
Cully et al.

(10) Patent No.: US 10,959,715 B2
(45) Date of Patent: Mar. 30, 2021

(54) DEVICES AND METHODS RELATED TO DEPOSITED SUPPORT STRUCTURES

(71) Applicant: W. L. Gore & Associates, Inc., Newark, DE (US)

(72) Inventors: Edward H. Cully, Flagstaff, AZ (US); Sherif A. Eskaros, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 404 days.

(21) Appl. No.: 14/435,081

(22) PCT Filed: Oct. 30, 2013

(86) PCT No.: PCT/US2013/067432
§ 371 (c)(1),
(2) Date: Apr. 10, 2015

(87) PCT Pub. No.: WO2014/070847
PCT Pub. Date: May 8, 2014

(65) Prior Publication Data
US 2015/0265391 A1    Sep. 24, 2015

Related U.S. Application Data

(63) Continuation-in-part of application No. 14/066,382, filed on Oct. 29, 2013, now Pat. No. 9,700,441.
(Continued)

(51) Int. Cl.
*A61B 17/00* (2006.01)
*A61L 31/14* (2006.01)
(Continued)

(52) U.S. Cl.
CPC ............ *A61B 17/0057* (2013.01); *A61F 2/07* (2013.01); *A61L 31/048* (2013.01); *A61L 31/088* (2013.01);
(Continued)

(58) Field of Classification Search
CPC ............... A61F 2/82; A61F 2/06; A61L 29/00
(Continued)

(56) References Cited

U.S. PATENT DOCUMENTS 3,874,388 A   4/1975 King et al.
4,762,129 A   8/1988 Bonzel
(Continued)

FOREIGN PATENT DOCUMENTS

CN   1725988 A    1/2006
EP   2478868 A1   7/2012
(Continued)

OTHER PUBLICATIONS

Annex to Form PCT/ISA/206 Communication Relating to the Results of the Partial International Search Report for PCT/US2013/067432 dated Feb. 6, 2014, corresponding to U.S. Appl. No. 14/066,382, pp. 1-3.
(Continued)

*Primary Examiner* — Dah-Wei D. Yuan
*Assistant Examiner* — Andrew J Bowman (57) ABSTRACT

The present disclosure describes medical devices comprising a bio-corrodible stent member and a graft member. The bio-corrodible stent member can comprise a metal applied directly to the graft member via a vapor deposition process, such as a chemical or physical vapor deposition process.

14 Claims, 5 Drawing Sheets

Related U.S. Application Data (60) Provisional application No. 61/720,938, filed on Oct. 31, 2012.

(51) Int. Cl.

| | | |
|---|---|---|
| *A61F 2/07* | (2013.01) | |
| *A61L 31/04* | (2006.01) | |
| *C23C 14/20* | (2006.01) | |
| *C23C 14/04* | (2006.01) | |
| *A61L 31/08* | (2006.01) | |
| *A61F 2/04* | (2013.01) | |

(52) U.S. Cl.
CPC .......... *A61L 31/148* (2013.01); *C23C 14/042* (2013.01); *C23C 14/20* (2013.01); *A61B 2017/0061* (2013.01); *A61B 2017/00526* (2013.01); *A61B 2017/00597* (2013.01); *A61B 2017/00659* (2013.01); *A61B 2017/00778* (2013.01); *A61B 2017/00818* (2013.01); *A61F 2002/045* (2013.01); *A61F 2002/072* (2013.01); *A61F 2210/0004* (2013.01); *A61F 2210/0076* (2013.01); *A61F 2220/0058* (2013.01); *A61F 2230/0069* (2013.01); *A61F 2240/001* (2013.01); *A61F 2250/0069* (2013.01)

(58) Field of Classification Search
USPC ...................................... 623/1.38, 1.16, 1.34
See application file for complete search history.

(56) References Cited

U.S. PATENT DOCUMENTS

| | | | |
|---|---|---|---|
| 5,040,548 A | 8/1991 | Yock | |
| 5,061,273 A | 10/1991 | Yock | |
| 5,476,589 A | 12/1995 | Bacino | |
| 5,486,193 A | 1/1996 | Bourne et al. | |
| 5,607,463 A | 3/1997 | Schwartz et al. | |
| 5,626,599 A | 5/1997 | Bourne et al. | |
| 5,733,294 A | 3/1998 | Forber et al. | |
| 5,814,405 A | 9/1998 | Branca et al. | |
| 6,080,182 A | 6/2000 | Shaw et al. | |
| 6,165,197 A | 12/2000 | Yock | |
| 6,171,329 B1 | 1/2001 | Shaw et al. | |
| 6,254,632 B1* | 7/2001 | Wu .......................... | A61F 2/91 623/1.15 |
| 6,355,052 B1 | 3/2002 | Neuss et al. | |
| 6,488,706 B1 | 12/2002 | Solymar | |
| 6,506,204 B2 | 1/2003 | Mazzocchi | |
| 6,537,310 B1 | 3/2003 | Palmaz | |
| 6,589,265 B1 | 7/2003 | Palmer et al. | |
| D493,223 S | 7/2004 | Solymar | |
| 7,704,268 B2 | 4/2010 | Chanduszko | |
| 8,246,762 B2 | 8/2012 | Janko et al. | |
| 9,700,441 B2 | 7/2017 | Cully | |
| 2001/0032013 A1* | 10/2001 | Marton ................... | A61F 2/915 623/1.15 |
| 2003/0023265 A1 | 1/2003 | Forber | |
| 2003/0149463 A1 | 8/2003 | Solymar et al. | |
| 2004/0073242 A1 | 4/2004 | Chanduszko | |
| 2004/0176799 A1 | 9/2004 | Chanduszko et al. | |
| 2005/0273119 A1 | 12/2005 | Widomski et al. | |
| 2006/0122646 A1 | 6/2006 | Corcoran et al. | |
| 2006/0217761 A1 | 9/2006 | Opolski | |
| 2006/0229711 A1* | 10/2006 | Yan .......................... | A61F 2/02 623/1.38 |
| 2006/0241687 A1 | 10/2006 | Glaser et al. | |
| 2007/0118176 A1 | 5/2007 | Opolski et al. | |
| 2007/0167980 A1 | 7/2007 | Figulla et al. | |
| 2008/0033475 A1 | 2/2008 | Meng | |
| 2009/0012559 A1 | 1/2009 | Chanduszko | |
| 2009/0099647 A1 | 4/2009 | Glimsdale et al. | |
| 2009/0228038 A1 | 9/2009 | Amin | |
| 2009/0292310 A1 | 11/2009 | Chin et al. | |
| 2010/0057195 A1 | 3/2010 | Roeder et al. | |
| 2010/0076544 A1 | 3/2010 | Hoffmann | |
| 2010/0191323 A1* | 7/2010 | Cox ......................... | A61F 2/07 623/1.38 |
| 2010/0324538 A1 | 12/2010 | Van Orden | |
| 2011/0112547 A1 | 5/2011 | Uihlein et al. | |
| 2011/0166593 A1 | 7/2011 | Paul, Jr. | |
| 2011/0238156 A1* | 9/2011 | Tischler ................... | A61F 2/915 623/1.16 |
| 2012/0071918 A1 | 3/2012 | Amin et al. | |
| 2012/0078295 A1 | 3/2012 | Steiner et al. | |
| 2012/0091809 A1 | 4/2012 | Mueller et al. | |
| 2012/0143242 A1 | 6/2012 | Masters | |
| 2012/0165919 A1 | 6/2012 | Cox et al. | |
| 2012/0283768 A1 | 11/2012 | Cox et al. | |
| 2013/0073029 A1 | 3/2013 | Shaw | |
| 2013/0138138 A1 | 5/2013 | Clark et al. | |
| 2014/0018841 A1 | 1/2014 | Peiffer et al. | |
| 2014/0031928 A1 | 1/2014 | Murphy et al. | |
| 2014/0142610 A1 | 5/2014 | Larsen et al. | |
| 2014/0142617 A1 | 5/2014 | Larsen et al. | |

FOREIGN PATENT DOCUMENTS

| | | |
|---|---|---|
| WO | 96/32882 A1 | 10/1996 |
| WO | 01/74274 | 10/2001 |
| WO | 02/056790 | 7/2002 |
| WO | WO-2005084583 A2 | 9/2005 |
| WO | WO-20060099470 A2 | 3/2006 |
| WO | WO-2007089912 A2 | 8/2007 |
| WO | 2008/041225 A2 | 4/2008 |
| WO | WO-2008083190 A2 | 7/2008 |

OTHER PUBLICATIONS

International Search Report for PCT/US2013/067432 dated Jun. 12, 2014, corresponding to U.S. Appl. No. 14/066,382, pp. 7.

Durmoo et al. Biocorrosion of Stainless Steel Grade 304L (SS304L) in Sugar Cane Juice, Electrochimica Acta 54 (2008) pp. 74-79.

Majid et al. Analysis of In Vivo Corrosion of 316L Stainless Steel Posterior Thoracolumbar Plate Systems; A Retrieval Study, J Spinal Disord Tech 2011;24:500-505.

European Search Report from 17185101.7, dated Nov. 2, 2017, 8 pages.

International Preliminary Report on Patentability received for PCT Patent Application No. PCT/US2013/067432, dated May 14, 2015, 9 pages.

International Search Report and Written Opinion for PCT/US2013/067510, dated Feb. 13, 2014, 12 pages.

International Search Report and Written Opinion for PCT/US2013/070371, dated May 16, 2014, 29 pages.

International Written Opinion received for PCT Patent Application No. PCT/US13/067432, dated Jun. 12, 2014, 7 pages.

\* cited by examiner

DEVICES AND METHODS RELATED TO DEPOSITED SUPPORT STRUCTURES

FIELD

The present disclosure relates generally to implantable, bio-corrodible devices and, more specifically, to medical devices comprising bio-corrodible metal stent members formed on a graft member.

BACKGROUND

Implantable medical devices are frequently used to treat the anatomy of patients. Such devices can be permanently, semi-permanently, or temporarily implanted in the anatomy to provide treatment to the patient.

In many cases, the device may comprise one or more components that are designed to provide treatment for a sufficient period, then to corrode and/or dissolve and be absorbed by or otherwise incorporated into the body. For example, an implantable stent-graft may comprise a stent component designed to be absorbed by or otherwise incorporated into the body after providing reinforcement to a vessel for a sufficiently long treatment period.

Accordingly, there is a need for medical devices that feature one or more components that can be easily and safely absorbed or incorporated by the body, in a predictable manner, after sufficiently long treatment time has elapsed.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

DETAILED DESCRIPTION OF THE ILLUSTRATED EMBODIMENTS

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

As used herein, "medical devices" can include, for example, stents, grafts, filters, valves, occluders, fasteners, supports, sensors, markers, therapeutic agent delivery devices, and other endoluminal and implantable devices that are implanted, acutely or chronically, in the vasculature, gastrointestinal tract, cranium, or other body lumen or cavity at a treatment region.

The medical devices and/or medical device components comprising metallic materials as described herein can be bio-corrodible. As used herein, "bio-corrodible" means the ability for the metallic portions of a medical device to absorb, resorb, corrode, fracture, dissolve, degrade, and/or disintegrate partially or fully over time while residing inside a patient and when exposed to a physiological environment, which can include fluids, electrolytes and dissolved gasses such as hydrogen ions, chloride ions, sodium ions, potassium ions, bicarbonate, phosphate, blood, lymph, proteins, amino acids, plasma, oxygen, carbon dioxide, and the like. Bio-corrosion may involve any combination of metal corrosion processes such as galvanic, pit, crevice, intra-granular, inter-granular, stress-corrosion cracking, corrosion fatigue, fretting corrosion, and the like. Bio-corrosion may comprise any combination and degree of uniform and non-uniform disintegration, for example with accelerated or decelerated zones of corrosion, varying ratios of inter- to intra-grain corrosion, varying degrees of fragmentation of the device or elements of the device, and further corrosion of the fragments.

As used herein, "bioabsorbable" means the ability for a medical device comprising polymeric components to hydrolyze, corrode, degrade, dissolve, absorb, resorb, or otherwise assimilates into the body partially or fully over time while residing inside a patient and when exposed to a physiological environment, which can include water, electrolytes and dissolved gasses such as hydrogen ions, chloride ions, sodium ions, potassium ions, bicarbonate, phosphate, blood, lymph, proteins, amino acids, plasma, oxygen, carbon dioxide, and the like. For example, organic polymers such as polyesters may degrade in vivo by chemical transformations such as hydrolysis.

Figure 1:
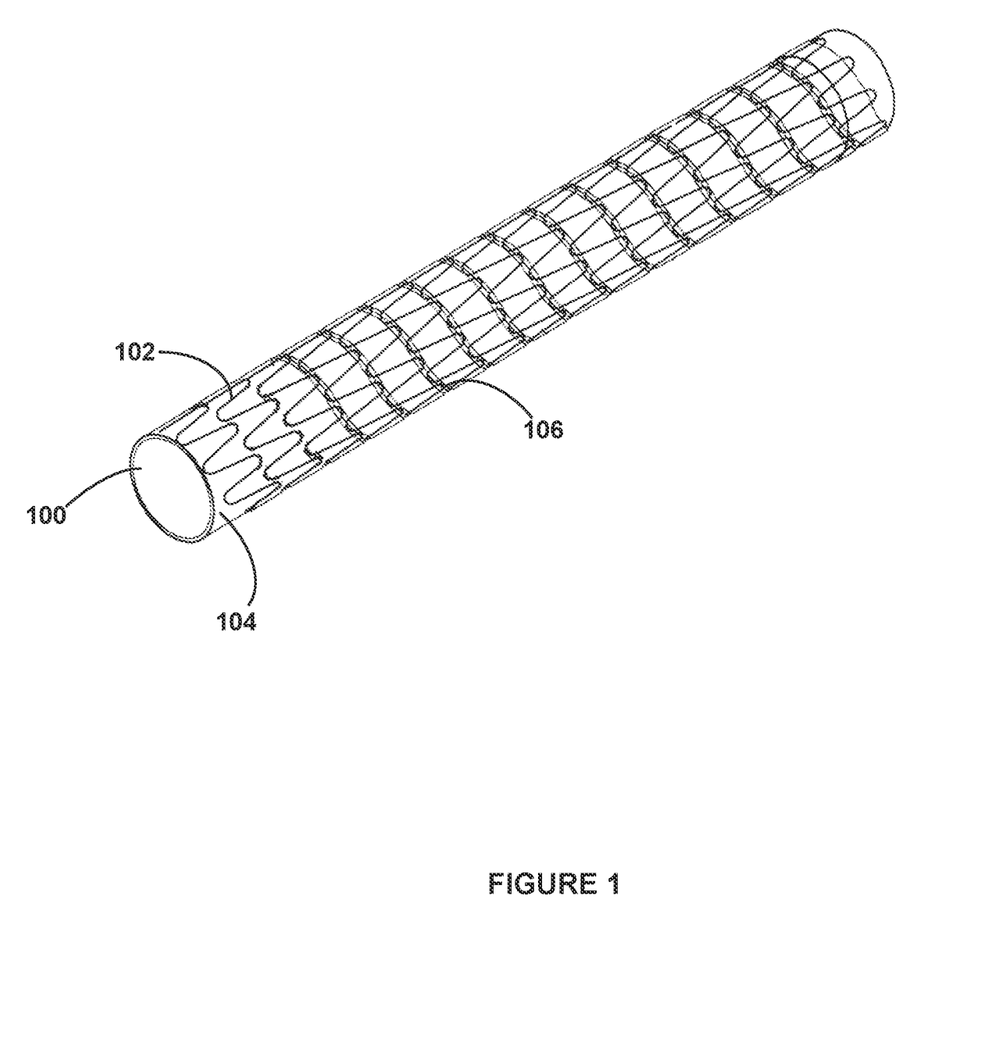
FIG. 1 illustrates a perspective view of a medical device in accordance with the present disclosure.

For example, with reference to FIG. 1, a medical device 100 in accordance with the present disclosure comprises a graft member 104 and a stent member 102 located about at least the proximal end of graft member 104. In various embodiments, graft member 104 comprises a polymeric membrane capable of sealing off a section of vessel wall, e.g. sealing perforations and ruptures, and/or correcting abnormalities, e.g., aneurysms, dissections, and fistulas, and/or to protecting a system from vessel wall lesions, e.g., preventing/minimizing the shedding of materials from lesions (e.g., plaque) into the bloodstream. Stent member 102 can comprise a structural framework that supports graft member 104 and/or a vessel. Device 100 can have a delivery profile configured to traverse a tortuous vasculature and capable of expansion to a nominal diameter. Device 100 can be balloon expandable or self-expanding.

Graft member 104 can comprise an interior and an exterior surface. In various embodiments, graft member 104 is configured such that stent member 102 is disposed on and concentrically surrounds at least a portion of the exterior surface. In such configurations, the interior surface of graft member 104 is exposed to the interior of the treatment area, such as, for example, a blood vessel. In an embodiment, graft member 104 can comprise a tubular form having a lumen extending there through. In various embodiments, the interior of graft member 104 is sufficiently impermeable to a fluid in order to prevent blood from passing through graft member 104.

In various embodiments, graft member 104 can comprise an exterior surface that allows for tissue in-growth. Facilitating in-growth permits graft member 104 to be incorporated into the vessel wall after a period. In an embodiment, the exterior surface of graft member 104 can comprise a material that has an open, porous microstructure. An open, microstructure provides an uneven surface topography having crevices, tunnels, and cavernous features within which cells and tissue(s) can occupy. Similarly, in other embodiments, the exterior surface can comprise an open macrostructure that can facilitate tissue in growth, e.g., a surface providing a lattice framework that provides an uneven surface topography with surface features within which cells and tissue(s) can occupy. In addition, the outer surface can be coated or treated with beneficial agents that enhance the rate of tissue in growth. For example, in an embodiment, a beneficial agent can comprise a pro-angeogenic agent, such as a vascular endothelial growth factor.

In various embodiments, stent member 102 can comprise a structural support that when expanded, does not completely cover graft member 104, leaving it partially exposed in a manner to facilitate tissue in-growth. In other embodiments, stent member 102 contributes a macrostructure having an uneven surface topography for in-growth.

Graft member 104 can comprise, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. Other embodiments for a graft member material can include high strength polymer fibers such as ultra high molecular weight polyethylene fibers (e.g., Spectra®, Dyneema Purity®, etc.), other polyethylenes such as Dacron®, or aramid fibers (e.g., Technora®, etc.). Embodiments of ePTFE for use in a graft are further described in U.S. Pat. No. 5,476,589 to Bacino and U.S. Pat. No. 5,814,405 to Branca et al. In an embodiment, graft member 104 can comprise a bioabsorbable organic material, such as poly(amino acids), poly(anhydrides), and the hydrolysable polyesters, such as poly(caprolactones), poly(lactic/glycolic acid), poly(hydroxybutyrates) and poly(orthoesters). Any graft member that is capable of providing a lumen for fluid flow within the body of a patient is within the scope of the present disclosure.

In some embodiments, stent member 102 is a structural framework configured to provide a desired amount of support to hold the lumen of graft member 104 radially open within a vessel. The stent member 102 can, for example, be supportive of graft member 104 long enough until tissue sufficiently in-grows into graft member 102. In other embodiments, stent member 102 provides support to graft member 104 until graft 104 is no longer needed, at which point graft 104 can be removed by, for example, excretion.

In an embodiment, stent member 102 is located along only a portion of graft member 102, such as the proximal end. In an embodiment, stent member 102 provides sufficient rigidity to the graft member so that it will not radially collapse or otherwise constrict the lumen upon deployment.

Accordingly, in various embodiments, stent member 102 is configured to provide a threshold level of support to a graft member 104 within a body lumen, such as a blood vessel for at least a specific period. The period for which the stent member 102 is to provide sufficient support to the graft member 104 can be referred to as a treatment period. The treatment period can correspond with, for example, the estimated time required for sufficient tissue in-growth within the graft member 104 to occur, thus obviating the need for the support provided by stent member 102. In other embodiments, the treatment period can correspond with the amount of time needed for graft member 104 to provide a fluid bypass, after which graft 104 can be removed by, for example, excretion.

To provide further structural support to the graft member 104, in various embodiments, the proximal end (in flow side) can have a securing mechanism to seat the proximal end to vessel wall, e.g., an anchor, barb, or other tissue-securing device. The securing mechanism can be configured to actuate upon expansion.

In an embodiment, device 100 can be suitable as an intracranial stent-graft. In an embodiment, device 100 can comprise a thin, wispy graft member 104, e.g., a tubular form having a nominal diameter of between about 2 mm to about 6 mm and wall thickness of less than about 6 µm to less than about 4 µm. A thin graft member 104 can comprise a lightweight structural framework to hold the lumen open in a vessel. The thickness and/or width of the features making up the stent member 102 can be between about 0.1 µm to about 1 mm, or more.

The present disclosure also contemplates stent member 102 can be a more robust structural framework configured to provide a desired amount of support to dilate a vessel or hold open a vessel. In various embodiments, stent member 102 is configured to provide a threshold level of support to a vessel, such as a blood vessel for a period sufficient for the supported tissue to remodel.

Stent member 102 can comprise a bio-corrodible material. In such configurations, after medical device 100 is deployed in the treatment area, stent member 102 begins to bio-corrode. As stent member 102 bio-corrodes, the amount of support provided to the graft member decreases. Eventually, stent member 102 can bio-corrode such that a desired level of support is no longer provided by stent member 102 to the treatment area. In embodiments intended to treat cerebral pathology such as aneurysms and those devices including a graft material, stent member 102 and optionally a securing mechanism merely needs to hold the graft material open and in place long enough for cellular in-growth to take place. In other words, the vessel itself may need no support; it is the graft member 104 component requiring temporary support to resist acute migration caused by shear forces of blood flow. Once tissue in-growth occurs, the minimal support provided by the stent member 102 is no longer required.

In a further embodiment, stent member 102 can be configured to bio-corrode in an approximated predictable manner after deployment to the treatment area. For example, stent member 102 can comprise a bio-corrodible material that bio-corrodes at an approximate predictable rate. In such embodiments, one or more of the pattern of stent member 102, material type, and/or its rate of corrosion to provide sufficient structure to a body lumen, such a blood vessel, for a desired treatment period. For example, physical attributes thickness and width of stent member features can be selected to provide sufficient support for the treatment period. In addition, increasing or decreasing the number of structural features, such as bands, struts, and/or tessellations, can be varied. Further tailoring includes, selecting a material that has high strength properties comparable to that of stainless steel can be used to construct a lightweight or delicate framework and yet still provide sufficient structural support to graft member. For example, the thickness of stent member 102 can be chosen such that stent member 102 provides sufficient support at the treatment area for at least the duration of the treatment period. Other physical attributes of stent member 102, such as the pattern and/or surface profile of stent member 102 can be selected to provide a predictable timeframe for bio-corrosion of stent member 102.

In various embodiments, one or more physical attributes of stent member 102 can be selected to provide sufficient support for a treatment period but also to account for long-term concerns over an implant present in certain treatment areas. For example, in cerebral suitable embodiments in, the thickness of stent member 102 can be minimized to prevent reducing the cross sectional profile of the vessel. Furthermore, in bio-corrodible embodiments in which a lightweight stent member is sufficiently supportive, the thickness of stent member 102 can be minimized to reduce the amount of degradation byproducts.

In various embodiments, the bio-corrodible material comprises a bio-corrodible metal or metal alloy. For example, stent member 102 can comprise iron, magnesium, zinc, tungsten, or an alloy of thereof. An iron alloy refers to a metal composition with iron (Fe) present as the major component. In various embodiments, an iron alloy may comprise a percent (by weight) iron concentration within the range of at least about 50% to at least about 95%. In addition to the elemental iron, iron alloys for use in stent member 102 can comprise non-iron elements such as carbon, nickel, cobalt, manganese, magnesium, lithium, calcium, chromium, molybdenum, tantalum, platinum, palladium, vanadium, iridium, rhenium, rhodium, rubidium, osmium, tungsten, titanium, niobium, zirconium, hafnium, aluminum, boron, sulfur, tin, silicon, yttrium, zinc, bismuth, silver, copper, iridium, indium, tin, and any lanthanide or actinide. In various embodiments, an iron alloy for stent member 102 can comprise from 0 to about 40% manganese, 0 to about 5% chromium, 0 to about 10% nickel, 0 to about 25% cobalt, 0 to about 1% aluminum, 0 to about 5% molybdenum, 0 to about 3% titanium, 0 to about 3% zirconium, 0 to about 1% carbon, 0 to about 1% silicon, 0 to about 3% niobium, 0 to about 1% nitrogen, and 0 to about 1% yttrium, with the remainder iron. Bio-corrodible iron alloys can lack those elements acknowledged as being beneficial in enhancing the corrosion resistance of iron, e.g., chromium, nickel, molybdenum, copper, titanium, vanadium, and silicon. Examples of iron alloys for use in stent member 102 can be found in U.S. Pat. No. 8,246,762 to Janko et al., the content of which is hereby incorporated by reference in its entirety. Notwithstanding the above, stent member 102 can comprise any bio-corrodible metal or metal alloy capable of providing temporary or semi-permanent support to a lumen within the body of a patient, such as a blood vessel.

In various embodiments, stent member 102 comprises a layer or pattern of bio-corrodible metal or metal alloy applied directly to a graft member, such as graft member 104. In various embodiments, the bio-corrodible metal or metal alloy can be applied to graft member 104 through a vapor deposition process, an electroless deposition, or other deposition process. Deposition technology enables the construction of a lightweight stent member with minimal metal for the desired level of structural support.

During vapor deposition, the process parameters, such as chamber pressure, deposition pressure, partial pressure of the process gases, the target temperature, bias voltage, substrate or source movement relative to the target, the number and type of substrates, and power are controlled to optimize deposition of the desired species onto the graft member 104. In further embodiments, once the initial layer is vapor deposited, additional layers can optionally be added through electroplating.

Alternatively or in addition thereto, a bioabsorbable polymer can be directly applied to graft member 104 or overlying stent member 102, also through a deposition process.

In order to construct device through a deposition process, graft member 104 can optionally comprise an exterior surface or a portion thereof that has been treated, coated, and/or constructed to facilitate adhesion of stent member 102 to graft member 104. In an embodiment, the portion of the exterior surface treated, coated, or constructed to facilitate adhesion can form a stent member 104 pattern. For example, the exterior surface of graft member 104 can be coated, whether continuously or discontinuously, with an adhesive, e.g., a biocompatible hot melt adhesive, in a stent member 102 pattern. A suitable adhesive can comprise a fluoropolymer adhesive, such as fluorinated ethylene propylene (FEP). By way of another example, the exterior surface can comprise an ePTFE layer with an open microstructure that provides a surface topography of varying heights. The uneven topography can be more amenable to stent member 102 adhesion. In an embodiment, the ePTFE material can comprise a node and fibril structure or substantially fibrillated structure. The size of the nodes and fibrils can be engineered to create a desired surface topography. In another example, the exterior surface can comprise inset channels that define the stent member 102 pattern; as such, the stent member 102 is inset, at least partially, into graft member 104.

In various embodiments, graft member 104 can comprise an exterior surface or a portion thereof that has been treated, coated, and/or constructed to provide protection to graft member 104 from degradation during the deposition process. In other embodiments, graft member 104 damage occurring because of a deposition process can result in a more uneven surface topography that can facilitate cellular in-growth as previously described. For example, plasma particles generated during a sputter coating process can inadvertently hit the substrate and result in a more reticulated, uneven surface topography.

In accordance with another aspect of the disclosure, the medical device can be delivered endovascularly, and thus, a delivery system can comprise medical device 100 as described herein mounted at or near the distal end of a catheter or guidewire about an expansion member and/or constrained with a constraining device. In an embodiment, expansion member is a balloon that is inflated at the treatment site to deploy medical device 100.

In an embodiment, the described medical device 100 can be constructed at the delivery diameter and can be crimped onto balloon. The delivery system can be introduced into the vasculature and tracked on a wire to the treatment site, e.g., at the site of a cerebral lesion. Once positioned, the balloon can be distended to a profile, which provides intimate contact with the vessel wall, which can cause the stent member 102 to plastically deform. The pressure required for such distension can be a low pressure in the embodiments where stent member 102 is a lightweight structural framework.

Figure 2:
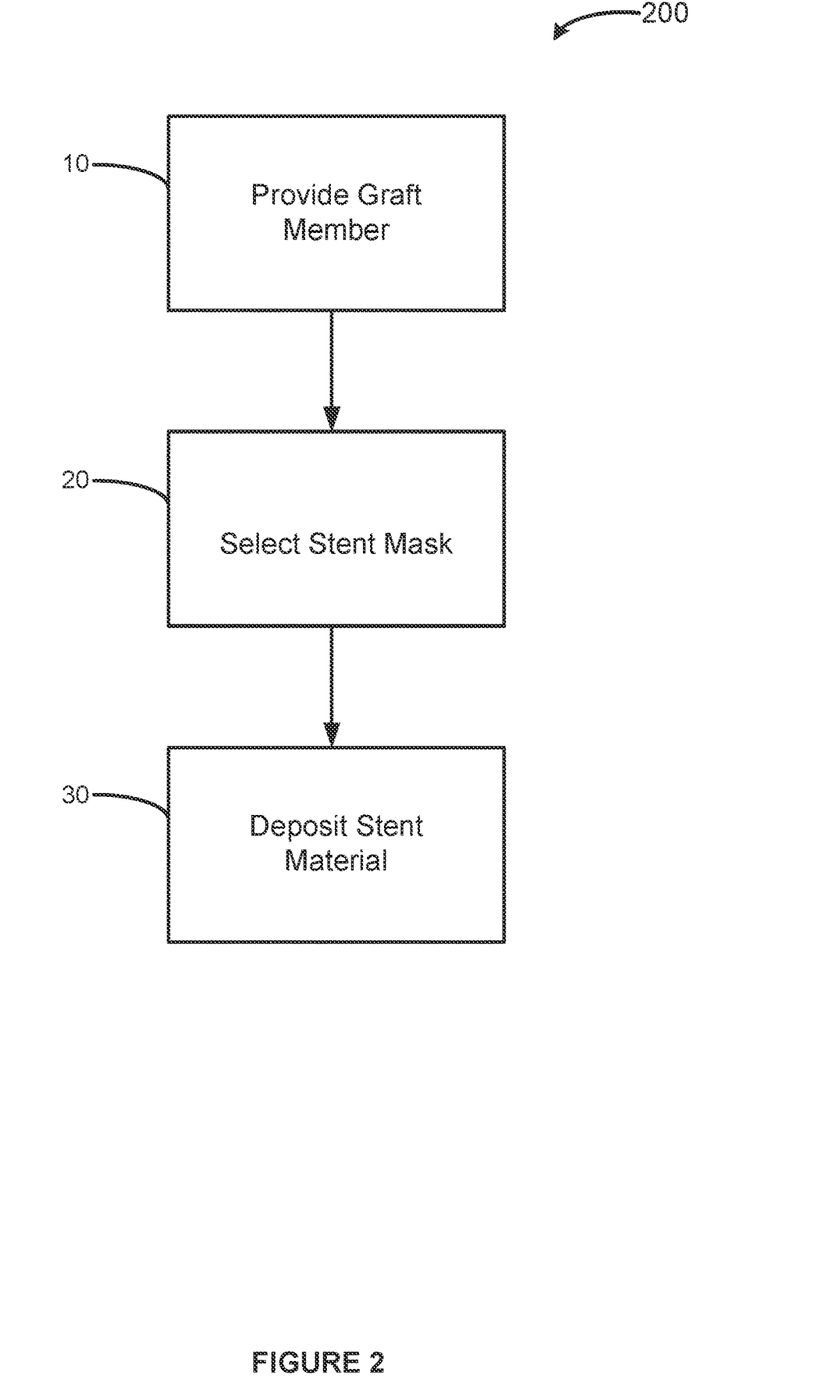
FIG. 2 illustrates a method for forming a medical device in accordance with the present disclosure.

With reference to FIG. 2, a method 200 for forming stent member 102 directly on the surface of graft member 104 using vapor deposition is illustrated. Method 200 comprises provide graft member step 10. Provide graft member step 10 comprises selecting a graft member suitable both for implantation in the anatomy of a patient and for receiving and supporting a bio-corrodible stent member, such as stent member 102. The graft member of step 10 can comprise graft member 104, as described above.

Figure 3A:
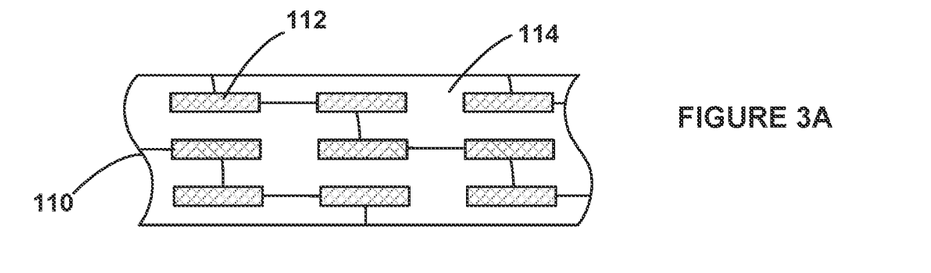
FIGS. 3A-3C illustrate various masks for use in forming a medical device in accordance with the present disclosure.
Figure 3B:
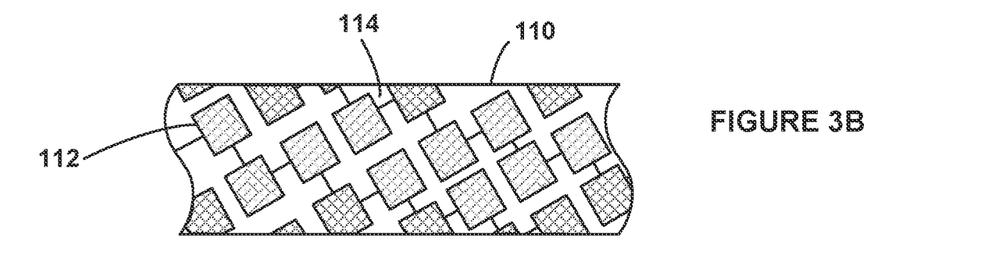
Figure 3C:
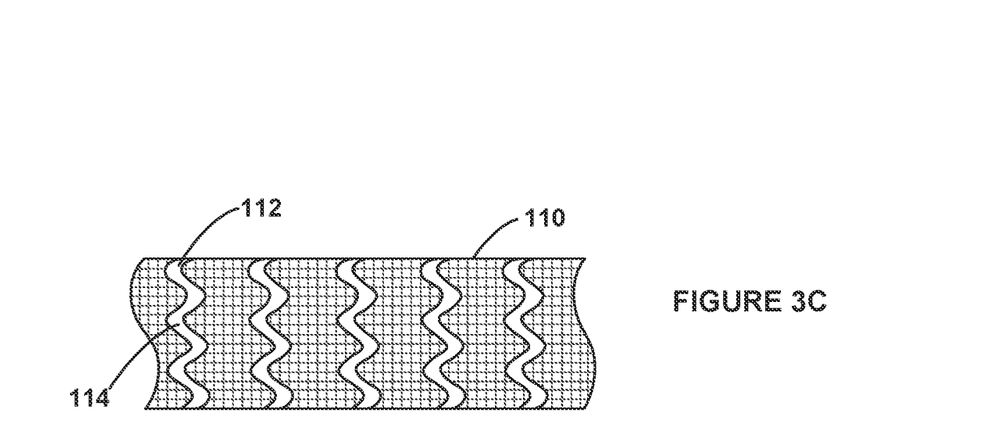

Method 200 further comprises a select stent mask step 20. Select mask step 20 comprises selecting a mask that corresponds with a desired pattern for stent member 102. The pattern can comprise an open-cell or closed-cell conformation. The pattern can comprise a series of adjacent bands, e.g., undulating rings, and interconnecting struts and/or a tessellated pattern. During use, bands can be expanded from an initial, small diameter to a larger diameter to contact the stent member 102 against a wall of a vessel, thereby maintaining the patency of the vessel. Struts can be utilized to vary the degree of stent member 102 flexibility and/or conformability that allow the stent member 102 to adapt to the contours of the vessel. With reference to FIGS. 3A-3C, various masks 110 are illustrated. In various embodiments, masks 110 comprise a cylinder capable of concentrically surrounding at least a portion of graft member 104. Each mask 110 comprises a pattern 112. In various embodiments, pattern 112 comprises the inverse of the desired structure of stent member 102. However, any mask capable of forming a desired pattern in a stent member 102 is within the scope of the present disclosure. Once selected, mask 110 can be applied to graft member 104 such that it concentrically surrounds at least a portion of graft member 104.

Method 200 further comprises a deposit stent material step 30. In various embodiments, deposit stent material step 30 comprises exposing graft member 104 to a substrate deposition process. The substrate deposition process can be any process that sufficiently preserves the graft member's mechanical and chemical performance properties while depositing the structural framework to the graft member 104. Deposition processes can include sputter deposition, resistive thermal deposition, electron beam evaporation, or other suitable processes.

For example, deposit stent material step 30 comprises exposing the masked graft member 104 to a vapor deposition source. The vapor deposition source contains the bio-corrodible metal or metal alloy that will constitute stent member 102.

Stent member 102 is formed by the deposition of the desired bio-corrodible metal or metal alloy on the surface of graft member 104 exposed by mask 110. The bio-corrodible metal is deposited on the surface of graft member 104 over an exposed region 114 of mask 110. The resulting stent member 102 comprises a bio-corrodible metal or metal alloy in the general shape of pattern 112. After stent member 102 has been formed on the surface of graft member 104, mask 110 can be removed from graft member 104.

In some embodiments, graft member 104 can be coupled to a mandrel in preparation for exposure to a vapor deposition source. The mandrel can be configured to rotate and to be laterally displaced according to a desired pattern. The desired pattern can comprise, for example, a helical or undulating helical shape. By rotating and/or laterally displacing the mandrel and graft member 104 and/or the deposition source according to the desired pattern, metal or metal alloy from the deposition source is deposited along the surface of graft member 104 in the desired pattern. Once completed, graft member 104 and newly formed stent member 102 can be removed from the mandrel and prepared for implantation in the body of a patient.

In other embodiments, a deposition process can comprise an electroless deposition. Graft member can be dipped into a solution wherein metal will deposit on the catalytically active sites of the graft member. A catalytic reagent can be applied to the exterior surface of the graft member in a desired pattern to which the metal components within the solution will deposit. In an embodiment, an electroless solution can comprise iron, manganese, niobium, and carbon proportioned to create a high percentage manganese, iron alloy.

In various embodiments, post deposition processing, such as annealing, may also be required to obtain a stent member 102 of sufficient ductility to maintain structural support. Annealing can be localized to minimize the damaging effects to the graft member 104 that can be caused by increased temperatures.

Figure 4:
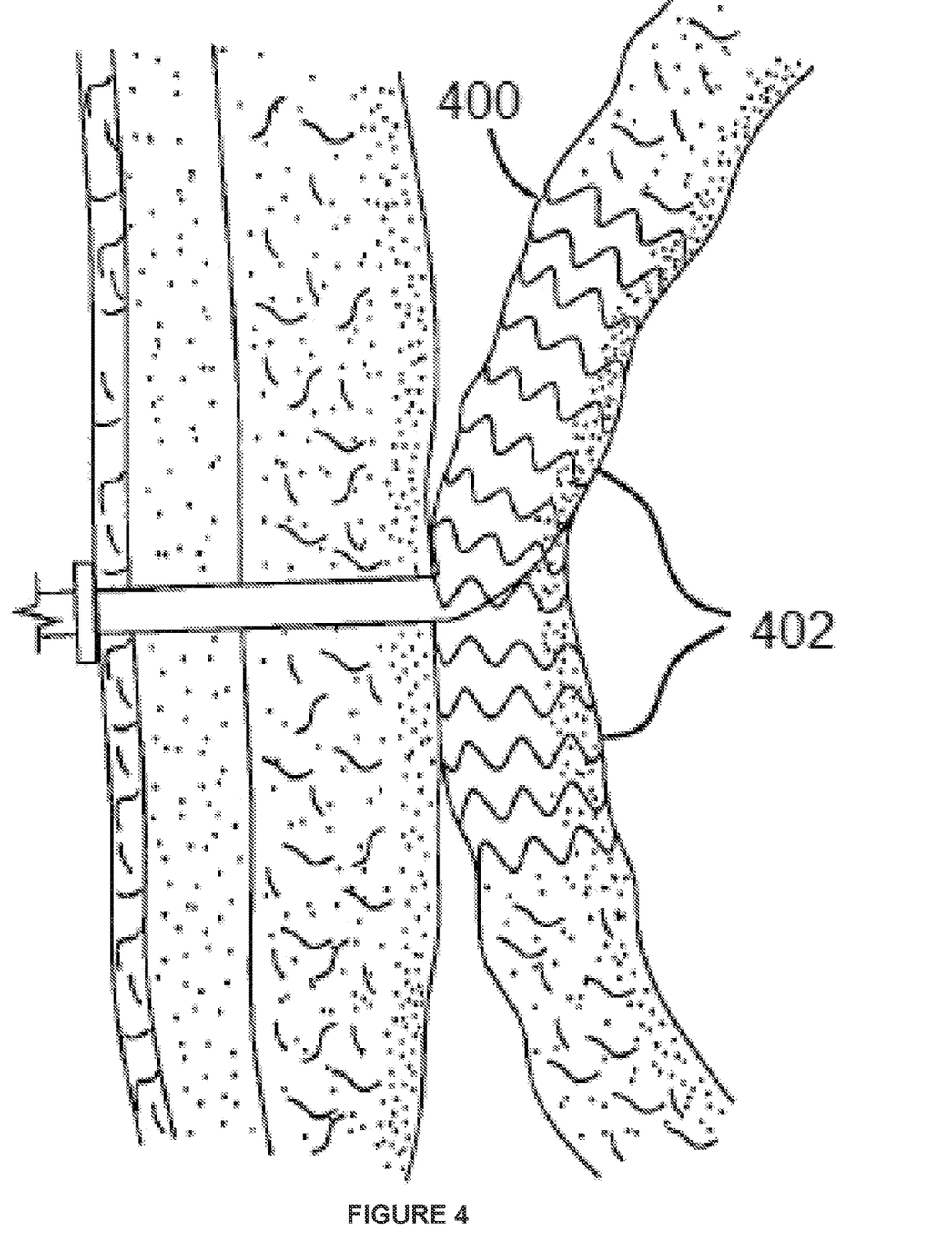
FIG. 4 illustrates another perspective view of a medical device in accordance with the present disclosure.

With reference to FIG. 4, medical device 400 comprises a bio-corrodible frame 402. Bio-corrodible frame 402 can comprise, for example, a stent configured to support a portion of an intestine in a colostomy or ileostomy procedure. Medical device 400 can further comprise a barrier disposed around at least a portion of bio-corrodible frame 402. In various embodiments, bio-corrodible frame 402 can provide support to the portion of the intestine for a desired treatment period. In such embodiments, after the treatment period, bio-corrodible frame 402 can be excreted.

Figure 5:
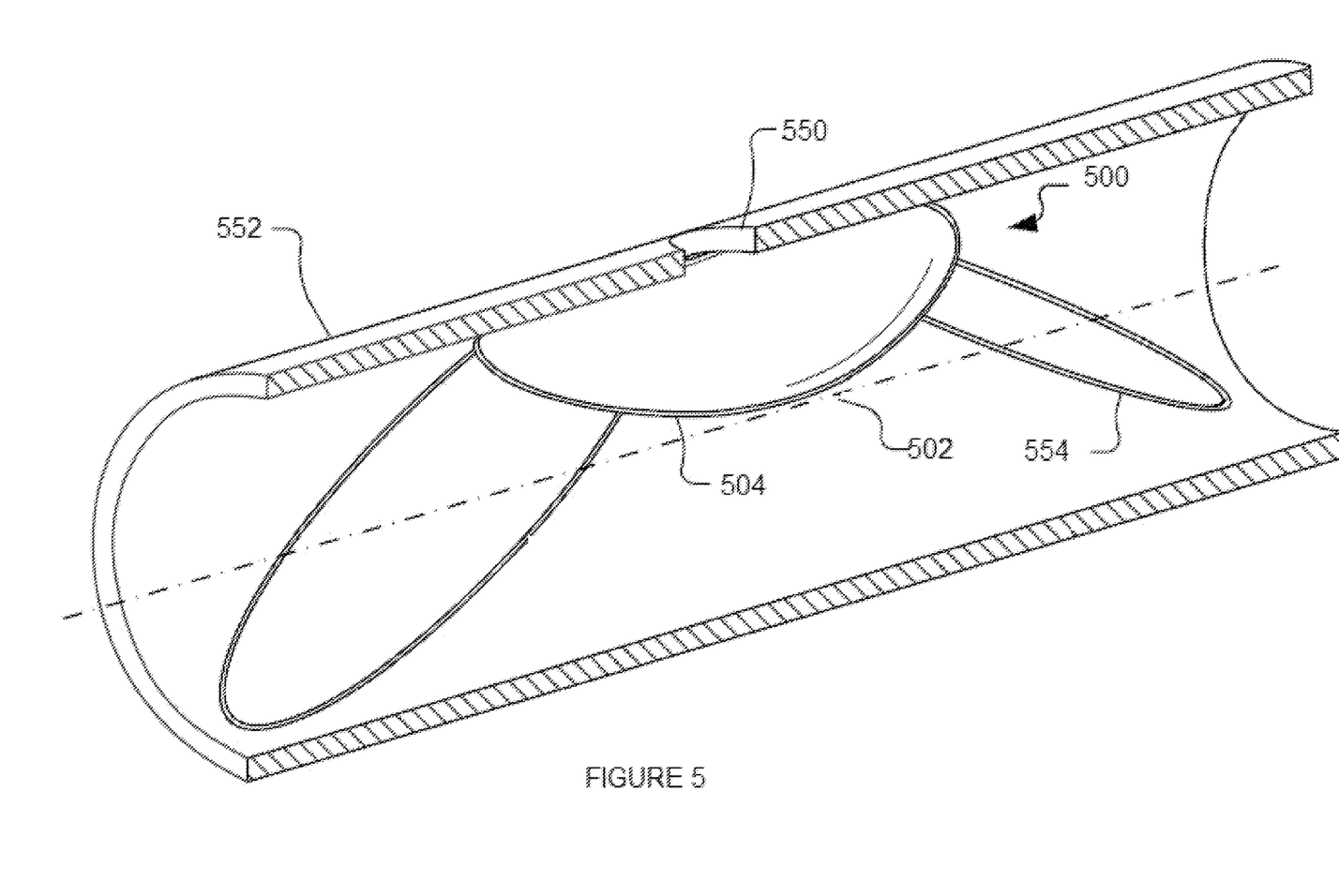
FIG. 5 illustrates a perspective view of yet another medical device in accordance with the present disclosure.

With reference to FIG. 5, medical device 500 comprises a bio-corrodible sealing frame 502 and a sealing membrane 504. In various embodiments, medical device 500 can be configured to seal an opening 550 in a lumen 552. In such embodiments, sealing membrane 504 can comprise a polymer that inhibits or reduces passage of blood, and other bodily fluids and materials. In some embodiments, sealing membrane 540 has a material composition and configuration that inhibits or prevents tissue ingrowth to sealing membrane 540. In some embodiments, sealing member 540 has a microporous structure that provides a tissue ingrowth scaffold for durable sealing and/or supplemental anchoring strength of the device. In various embodiments, sealing membrane 540 comprises a fluoropolymer, such as an expanded polytetrafluoroethylene (ePTFE) polymer. In other embodiments, sealing membrane 540 comprises a polyester, a silicone, a urethane, another biocompatible polymer, Dacron, bioabsorbable systems, copolymers, or combinations and subcombinations thereof.

In various embodiments, sealing frame 502 comprises at least two struts 554. In various embodiments, struts 554 are configured to press the combination of the sealing frame 502 and the sealing membrane 504 against the wall of lumen 552. In this general fashion, device 500 can be placed in a body lumen to seal a defect in the body lumen wall. In various embodiments, lumen 552 can comprise an intestine and opening 550 comprises an opening in the wall of the intestine. In some cases, the intestine may be the colon. In other embodiments, the body lumen may be a blood vessel. In particular cases, the defect may be an aneurysm in the blood vessel.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An assembly for manufacture of a medical device comprising:
   a polymeric membrane comprising expanded polytetrafluoroethylene configured such that a surface of the polymeric membrane is configured to encourage adhesion of particles to the polymeric membrane along a designated stent pattern, wherein the surface of the polymeric membrane includes inset channels into the surface;
   a mask concentrically surrounding at least a portion of the polymeric membrane and including an inverse pattern of the designated stent pattern; and
   a bio-corrodible metal support structure deposited along the polymeric membrane along the designated stent pattern via a deposition process.

2. The assembly for manufacture of the medical device of claim 1, wherein the polymeric membrane is a graft.

3. The assembly for manufacture of the medical device of claim 2, wherein the medical device is a stent-graft.

4. The assembly for manufacture of the medical device of claim 1, wherein the support structure is a frame that comprises a sealing frame and the membrane comprises a sealing membrane, and wherein the device is implanted in the gastrointestinal tract.

5. The assembly for manufacture of the medical device of claim 1, wherein the medical device is used in one of a colostomy and an ileostomy procedure.

6. An assembly for manufacture of a stent-graft comprising:
   a tubular graft member comprising expanded polytetrafluoroethylene, the tubular graft member having a wall defining a luminal surface and an exterior surface, wherein the tubular graft member is configured such that the exterior surface of the wall is configured to encourage adhesion of a bio-corrodible metal along a designated stent pattern through a deposition process;
   a masking member concentrically surrounding at least a portion of the tubular graft member and including an inverse pattern of the designated stent pattern; and
   a bio-corrodible metal stent member circumferentially and axially disposed over the exterior surface along the designated stent pattern via a deposition process.

7. The assembly for manufacture of the stent-graft of claim 6 wherein the bio-corrodible metal comprises iron and magnesium.

8. The assembly for manufacture of the medical device of claim 1, wherein the deposition process is one of a vapor deposition process and an electroless deposition process.

9. The assembly for manufacture of the medical device of claim 1, wherein the bio-corrodible support structure is a frame having a radial thickness of between 0.1 µm and 1 µm.

10. The assembly for manufacture of the stent-graft of claim 6, wherein the deposition process is one of a vapor deposition process and an electroless deposition process.

11. The assembly for manufacture of the stent-graft of claim 6, wherein bio-corrodible metal stent member has a radial thickness of between 0.1 µm and 1 mm.

12. An assembly for the manufacture of a medical device comprising:
   a polymeric membrane having a surface that has been modified to include inset channels that define a designated stent pattern;
   a masking member concentrically surrounding at least a portion of the polymeric membrane and forming an inverse pattern, wherein the inverse pattern is inverse of the designated stent pattern; and
   a bio-corrodible metal frame coupled to the polymeric membrane such that the frame resides within the inset channels, wherein the frame is applied to the polymeric membrane via a deposition process.

13. The assembly for manufacture of the medical device of claim 12, wherein the deposition process is one of a vapor deposition process and an electroless deposition process.

14. The assembly for manufacture of the medical device of claim 12, wherein bio-corrodible metal frame has a radial thickness of between 0.1 µm and 1 mm.

* * * * *